(12) United States Patent
Kwon et al.

(10) Patent No.: US 11,298,086 B2
(45) Date of Patent: Apr. 12, 2022

(54) APPARATUS AND METHOD FOR ESTIMATING BLOOD PRESSURE

(71) Applicant: SAMSUNG ELECTRONICS CO., LTD., Suwon-si (KR)

(72) Inventors: Ui Kun Kwon, Hwaseong-si (KR); Chang Soon Park, Chungju-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 346 days.

(21) Appl. No.: 16/409,128

(22) Filed: May 10, 2019

(65) Prior Publication Data

US 2020/0107789 A1 Apr. 9, 2020

(30) Foreign Application Priority Data

Oct. 5, 2018 (KR) .................. 10-2018-0118825

(51) Int. Cl.
*A61B 5/029* (2006.01)
*A61B 5/00* (2006.01)
*A61B 5/02* (2006.01)
*A61B 5/021* (2006.01)

(52) U.S. Cl.
CPC ........ *A61B 5/7278* (2013.01); *A61B 5/02007* (2013.01); *A61B 5/029* (2013.01); *A61B 5/02116* (2013.01); *A61B 2560/0223* (2013.01)

(58) Field of Classification Search
CPC .............. A61B 5/7278; A61B 5/02007; A61B 5/02116; A61B 5/029; A61B 2560/0223
See application file for complete search history.

(56) References Cited

U.S. PATENT DOCUMENTS

| 8,343,062 | B2 | 1/2013 | Fortin et al. |
| 8,814,800 | B2 | 8/2014 | Fortin et al. |
| 2008/0255463 | A1 | 10/2008 | Chowienczyk et al. |
| 2009/0018422 | A1 | 1/2009 | Banet et al. |
| 2010/0160797 | A1 | 6/2010 | Banet et al. |

(Continued)

FOREIGN PATENT DOCUMENTS

| EP | 3117766 A1 | 1/2017 |
| KR | 10-2012-0006440 A | 1/2012 |

(Continued)

OTHER PUBLICATIONS

Yongwoo Park and José Azaña, "Optical signal processors based on a time-spectrum convolution," Opt. Lett. 35, 796-798 (Year: 2010).*

(Continued)

*Primary Examiner* — Patrick Fernandes
*Assistant Examiner* — Liam A Wallace
(74) *Attorney, Agent, or Firm* — Sughrue Mion, PLLC

(57) ABSTRACT

An apparatus for estimating blood pressure is provided. The apparatus for estimating blood pressure may include: a bio-signal measurer configured to measure a bio-signal from a user; and a processor configured to extract one or more feature values from the bio-signal, to adjust a combination coefficient for combining the one or more feature values based on a reference value associated with vascular compliance, and to estimate blood pressure based on the adjusted combination coefficient, and the one or more feature values extracted from the bio-signal.

17 Claims, 12 Drawing Sheets

(56) References Cited

U.S. PATENT DOCUMENTS

| | | |
|---|---|---|
| 2011/0005918 A1 | 1/2011 | Akeson et al. |
| 2011/0105917 A1 | 5/2011 | Fortin et al. |
| 2012/0302902 A1 | 11/2012 | Shin |
| 2014/0142445 A1 | 5/2014 | Banet et al. |
| 2016/0242700 A1 | 8/2016 | Ferber et al. |
| 2017/0347901 A1 | 12/2017 | Shao et al. |
| 2017/0360314 A1 | 12/2017 | Proenca et al. |
| 2018/0020931 A1* | 1/2018 | Shusterman ....... A61B 5/02116 600/483 |
| 2018/0020991 A1 | 1/2018 | Aung et al. |
| 2018/0070837 A1 | 3/2018 | Huijbregts et al. |
| 2018/0199893 A1 | 7/2018 | Hubner |

FOREIGN PATENT DOCUMENTS

| | | |
|---|---|---|
| KR | 10-2017-0063416 A | 6/2017 |
| KR | 10-1746492 B1 | 6/2017 |
| KR | 10-2017-0099979 A | 9/2017 |
| WO | 2008/154647 A1 | 12/2008 |
| WO | 2011/051822 A1 | 5/2011 |
| WO | 2016138965 A1 | 9/2016 |
| WO | 2016146356 A1 | 9/2016 |
| WO | 2018/172958 A1 | 9/2018 |

OTHER PUBLICATIONS

S. Sun et al., "Systolic blood pressure estimation using PPG and ECG during physical exercise", Physiological Measurement, Institute of Physics Publishing, Bristol, GB, vol. 37, No. 12, Nov. 14, 2016, pp. 2154-2169, XP020310964. (16 pages total).

Hayato Fukushima et al., "Cuffless Blood Pressure Estimation using only Photoplethysmography based on Cardiovascular parameters", Engineering in Medicine and Biology Society (EMBC), 2013 35th Annual International Conference of the IEEE, IEEE, Jul. 3, 2013, pp. 2132-2135, XP032488256. (4 pages total).

Communication dated Oct. 29, 2019 issued by the European Patent Office in counterpart European Patent Application No. 19185522.0.

* cited by examiner

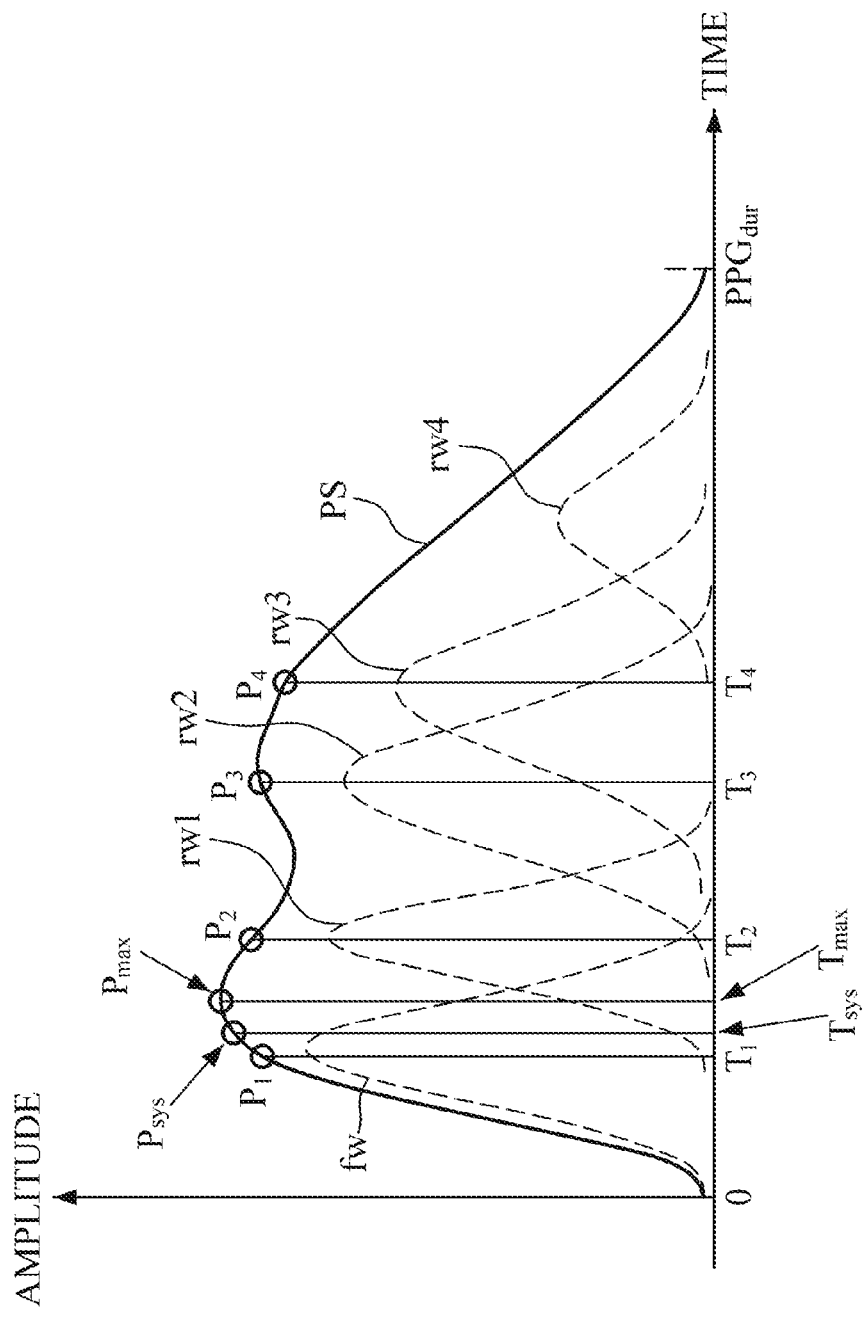

APPARATUS AND METHOD FOR ESTIMATING BLOOD PRESSURE

CROSS-REFERENCE TO RELATED APPLICATION(S)

This application is based on claims priority from Korean Patent Application No. 10-2018-0118825, filed on Oct. 5, 2018, in the Korean Intellectual Property Office, the disclosure of which is incorporated herein by reference in its entirety.

BACKGROUND

1. Field

Example embodiments of the present disclosure relate to an apparatus and method for cufflessly estimating blood pressure.

2. Description of the Related Art

Recently, with an aging population, soaring medical costs, and a lack of medical personnel for specialized medical services, research is being actively conducted on IT-medical convergence technologies, in which IT technology and medical technology are combined. Particularly, monitoring of the health condition of the human body is not limited to places such as hospitals, but is expanding to mobile healthcare fields that may monitor a user's health state anywhere and anytime in daily life at home or office. Typical examples of bio-signals, which indicate the health condition of individuals, include an electrocardiography (ECG) signal, a photoplethysmogram (PPG) signal, an electromyography (EMG) signal, and the like, and various bio-signal sensors are being developed to measure these signals in daily life. Particularly, a PPG sensor may estimate blood pressure of a human body by analyzing a shape of pulse waves which reflect a cardiovascular state and the like.

SUMMARY

According to an aspect of an example embodiment, there is provided an apparatus for estimating blood pressure, the apparatus including: a bio-signal measurer configured to measure a bio-signal from a user; and a processor configured to extract one or more feature values from the bio-signal, adjust a combination coefficient for combining the one or more feature values based on a reference value associated with vascular compliance, and estimate a blood pressure based on the adjusted combination coefficient and the one or more feature values extracted from the bio-signal.

The reference value may be obtained at a reference time including at least one of a calibration time of the bio-signal and a time at which the user is in a stable state.

The processor may be further configured to obtain, as the reference value, a maximum amplitude value of a reference bio-signal that is measured from the user at a reference time.

The processor may be further configured to: obtain a reference bio-signal including a first pulse waveform component and a second pulse waveform component, from the user at a reference time; and obtain, as the reference value, at least one of a ratio between a first amplitude value of a first pulse waveform component and a second amplitude value of a second pulse waveform component of the reference bio-signal, and a ratio between the first amplitude value and a maximum amplitude value of the reference bio-signal.

The reference value may include a vascular compliance index including an Augmentation Index.

The processor may be further configured to receive the vascular compliance index from an external device which measures the vascular compliance of the user.

The processor may be further configured to obtain the Augmentation Index by analyzing a waveform of a reference bio-signal that is measured from the user at reference time.

The processor may be further configured to obtain an adjustment value for adjusting the combination coefficient by inputting the reference value into a pre-defined adjustment value estimation equation.

The processor may be further configured to obtain the adjustment value by further inputting a statistical value of a plurality of reference values obtained from a plurality of other users, into the adjustment value estimation equation.

The one or more feature values may include a first feature value associated with cardiac output and a second feature value associated with total peripheral resistance.

The processor may be further configured to obtain at least one information of heart rate information, an area under the waveform of the bio-signal, time and amplitude values of a maximum point of the bio-signal, time and amplitude values of a minimum point of the bio-signal, and amplitude and time values of pulse waveform components included in the bio-signal, and extract the one or more feature values based on the at least one information.

The processor may be further configured to obtain a first variation in the first feature value compared to a first reference feature value, and a second variation in the second feature value compared to a second reference feature value, obtain a third variation based on the first variation and second variation, and estimate the blood pressure based on the first variation, the second variation, and the third variation.

The combination coefficient may be one of a plurality of combination coefficients. The processor may be further configured to adjust the plurality of combination coefficients corresponding to each of the first, the second, and the third variations, and combine the first, the second, and the third variations by multiplying the first, the second, and the third variations by the adjusted corresponding combination coefficients, respectively. The processor may be further configured to estimate the blood pressure by applying a scaling factor to a resulting value of the combining the first, the second, and the third variations.

In accordance with an aspect of an example embodiment, there is provided a method of estimating blood pressure, the method including: measuring a bio-signal from a user; extracting one or more feature values from the bio-signal; adjusting a combination coefficient for combining the one or more feature values based on a reference value associated with vascular compliance; and estimating blood pressure based on the adjusted combination coefficient, and the one or more feature values extracted from the bio-signal.

The method may further include: obtaining, as the reference value, a maximum amplitude value of a reference bio-signal that is measured from the user at reference time.

The method may further include: obtaining a reference bio-signal including a first pulse waveform component and a second pulse waveform component, from the user at a reference time; and obtaining, as the reference value, at least one of a ratio between a first amplitude value of a first pulse waveform component and a second amplitude value of a second pulse waveform component of the reference bio-signal, and a ratio between the first amplitude value and a maximum amplitude value of the reference bio-signal.

The adjusting the combination coefficient may include obtaining an adjustment value for adjusting the combination coefficient by inputting the reference value into a predefined adjustment value estimation equation.

The adjusting the combination coefficient may include obtaining the adjustment value by further inputting a statistical value of a plurality of values obtained from a plurality of other users, into the adjustment value estimation equation.

The one or more feature values may include a first feature value associated with cardiac output and a second feature value associated with total peripheral resistance.

BRIEF DESCRIPTION OF THE DRAWINGS

The above and/or other aspects will be more apparent by describing certain embodiments, with reference to the accompanying drawings, in which:

FIGS. 3A, 3B, 3C, 3D, 3E, 3F, and 3G are diagrams explaining an example of estimating blood pressure;

DETAILED DESCRIPTION

Figure 1:
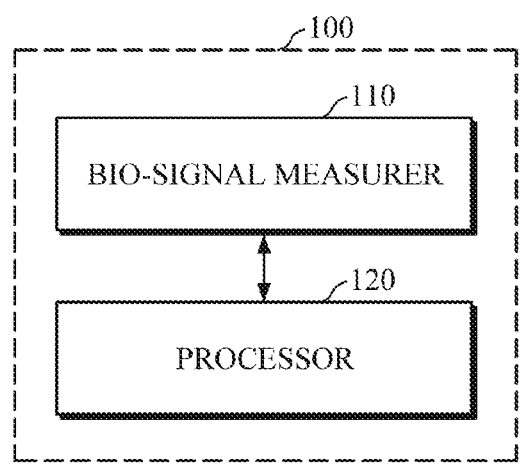
FIG. 1 is a block diagram illustrating an apparatus for estimating blood pressure according to an example embodiment.

Example embodiments are described in greater detail below with reference to the accompanying drawings.

In the following description, like drawing reference numerals are used for like elements, even in different drawings. The matters defined in the description, such as detailed construction and elements, are provided to assist in a comprehensive understanding of the example embodiments. However, it is apparent that the example embodiments can be practiced without those specifically defined matters. Also, well-known functions or constructions are not described in detail since they would obscure the description with unnecessary detail.

It will be understood that, although the terms first, second, etc. may be used herein to describe various elements, these elements should not be limited by these terms. These terms are only used to distinguish one element from another. Any references to singular may include plural unless expressly stated otherwise. In addition, unless explicitly described to the contrary, an expression such as "comprising" "including" will be understood to imply the inclusion of stated elements but not the exclusion of any other elements. Also, the terms, such as 'part' or 'module', etc., should be understood as a unit that performs at least one function or operation and that may be embodied as hardware, software, or a combination thereof.

Expressions such as "at least one of," when preceding a list of elements, modify the entire list of elements and do not modify the individual elements of the list. For example, the expression, "at least one of a, b, and c," should be understood as including only a, only b, only c, both a and b, both a and c, both b and c, all of a, b, and c, or any variations of the aforementioned examples.

Hereinafter, example embodiments of an apparatus and method for estimating blood pressure will be described in detail with reference to the accompanying drawings. The blood pressure estimating apparatus according to one or more example embodiments may be embedded in a terminal, such as a smartphone, a tablet PC, a desktop computer, a laptop computer, and the like, or may be manufactured as an independent hardware device. In this case, the independent hardware device may be a wearable device worn on an object, and examples thereof include a wristwatch-type wearable device, a bracelet-type wearable device, a wristband-type wearable device, a ring-type wearable device, a glasses-type wearable device, a hairband-type wearable device, or the like, but is not limited thereto.

Figure 2:
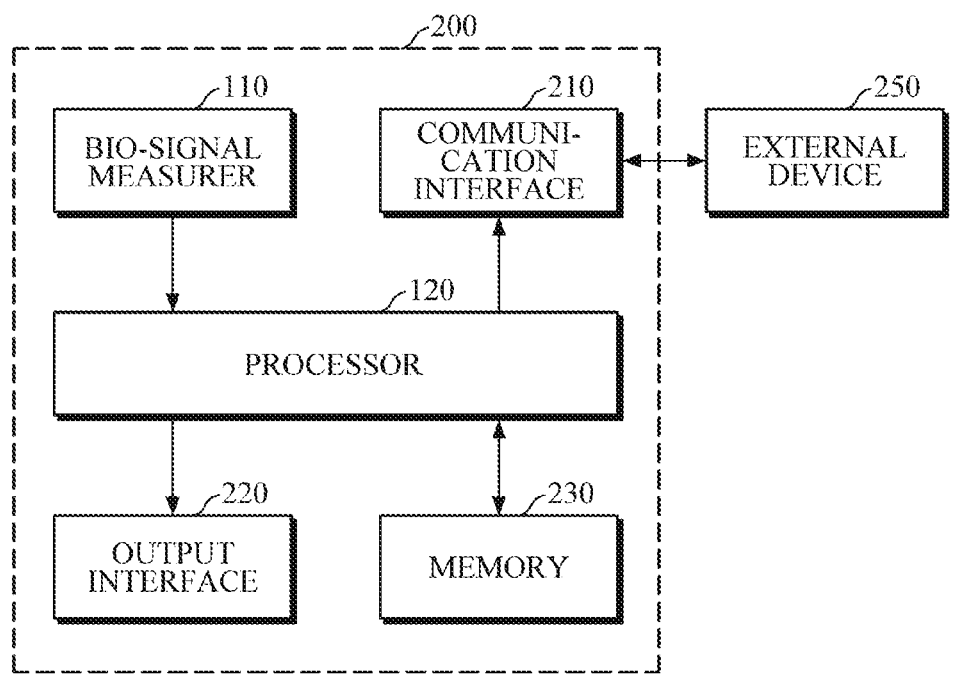
FIG. 2 is a block diagram illustrating an apparatus for estimating blood pressure according to another example embodiment.

FIG. 1 is a block diagram illustrating an apparatus for estimating blood pressure according to an example embodiment. FIG. 2 is a block diagram illustrating an apparatus for estimating blood pressure according to another example embodiment. FIGS. 3A to 3G are diagrams explaining an example of estimating blood pressure.

Referring to FIGS. 1 and 2, the blood pressure estimating apparatuses 100 and 200 include a bio-signal measurer 110 and a processor 120.

The bio-signal measurer 110 includes one or more sensors, and may measure various bio-signals from an object using the sensors. In particular, the one or more sensors may be sensors for measuring a photoplethysmogram (PPG) signal, an electrocardiography (ECG) signal, an electromyography (EMG) signal, a ballistocardiogram (BCG) signal, and the like, but are not limited thereto. Examples of the bio-signal measurer 110 may include an optical sensor, a spectrometer, a PPG sensor, an ECG sensor, an EMG sensor, and a BCG sensor.

The object may be a body part which comes into contact with or is adjacent to the bio-signal measurer 110, and may be a body part where pulse waves may be easily measured. For example, the object may be an area of skin on the wrist that is adjacent to the radial artery or a human skin area through which veins or capillaries pass. However, the object is not limited thereto, and may be peripheral body portions, such as fingers, toes, and the like, which have a high density of blood vessels.

The bio-signal measurer 110 may include a light source which emits light onto an object, and a detector which detects light scattered or reflected from the object. The light source may include a light emitting diode (LED), a laser diode, a fluorescent body, and the like, and may be formed as one or two or more arrays. The detector may include one pixel or a pixel array including two or more pixels, each of which may include a photo diode, a photo transistor, an image sensor, and the like which detect light and convert the detected light signal into an electric signal, but the detector is not limited thereto.

The processor 120 may be electrically connected to the bio-signal measurer 110. In response to a request for estimating blood pressure, the processor 120 may control the bio-signal measurer 110, and may receive a bio-signal from the bio-signal measurer 110. The request for estimating blood pressure may be input by a user or may be generated at predetermined intervals. Upon receiving an electrical bio-signal from the bio-signal measurer 110, the processor 120 may perform a preprocessing process, such as filtering for removing noise, amplifying a bio-signal, converting a bio-signal into a digital signal, and the like.

A variation in Mean Arterial Pressure (MAP) may be proportional to cardiac output (CO) and total peripheral resistance (TPR), as represented by the following Equation 1.

$$\Delta MAP = CO \times TPR \quad \text{[Equation 1]}$$

Herein, $\Delta$MAP denotes a difference in MAP between the left ventricle and the right atrium, in which MAP of the right atrium is generally in a range of 3 mmHg to 5 mmHg, such that MAP of the right atrium is similar to MAP of the left ventricle or MAP of the upper arm. Under a condition where absolute actual CO and TPR values are known, MAP may be obtained from the aorta or the upper arm. However, it may be difficult to estimate absolute CO and TPR values based on a bio-signal.

In an example embodiment, the processor 120 may extract a feature value associated with cardiac output (CO) (hereinafter referred to as a "first feature value") from a bio-signal, and may extract a feature value associated with total peripheral resistance (TPR) (hereinafter referred to as a "second feature value") from the bio-signal. Here, the first feature value may be a feature value which shows an increasing/decreasing trend in proportion to an actual CO value which relatively increases/decreases when an actual TPR value does not change significantly compared to a reference TRP value that is measured while the user is in a stable state. Further, the second feature value may be a feature value which shows an increasing/decreasing trend in proportion to an actual TPR value which relatively increases/decreases when an actual/measured CO value does not change significantly compared to a reference CO value that is measured while the user is in a stable state.

For example, the processor 120 may extract the feature values by analyzing a waveform of the measured bio-signal. The processor 120 may obtain, from a bio-signal, feature values such as heart rate information, time and amplitude values of a maximum point of the bio-signal, time and amplitude values of a minimum point of the bio-signal, an area under a bio-signal waveform, amplitude and time values of pulse waveform components included in the bio-signal, information on an internally dividing point between the obtained values, and may extract feature values by using the obtained characteristic points. In this case, the pulse waveform components included in the bio-signal may be obtained by performing secondary differentiation on the bio-signal, and by detecting a local minimum point of the secondary differential signal.

Referring to FIG. 3A, the pulse wave signal PS is represented as a superposition of propagation waves, starting from the heart toward the distal end portions of the body or a branching point in the blood vessel, and reflection waves returning back from the distal end portions or the branching point in the blood vessel. FIG. 3A illustrates an example where a waveform of a pulse wave signal PS is formed by a superposition of five pulse waveform components (e.g., the propagation wave fw and the reflection waves rw1, rw2, rw3, and rw4).

The processor 120 may extract feature values from the pulse wave signal PS by analyzing the pulse waveform components fw, rw1, rw2, rw3, and rw4. For example, the processor 120 may use pulses up to the third constituent pulse to estimate blood pressure. Pulses after the third pulse may not be observed depending on individuals in some cases, and may be difficult to be found due to noise or have a low correlation with estimation of blood pressure.

For example, the processor 120 may extract, as characteristic points, times $t_1$, $t_2$, and $t_3$, and amplitudes $P_1$, $P_2$, and $P_3$ of a maximum point of the first to the third constituent pulse waveforms fw, rw1, and rw2. In this case, upon obtaining the pulse wave signal PS, the processor 120 may perform secondary differentiation on the obtained pulse wave signal PS, and may extract the times $T_1$, $T_2$, and $T_3$, and the amplitudes $P_1$, $P_2$, and $P_3$ of the maximum point of the first to the third constituent pulse waveforms fw, rw1, and rw2 by using the secondary differential signal. For example, by detecting a local minimum point from the secondary differential signal, the processor 120 may extract the times $T_1$, $T_2$, and $T_3$ corresponding to the local minimum point of the first to the third constituent pulse waveforms fw, rw1, and rw2, and may extract amplitudes $P_1$, $P_2$, and $P_3$ corresponding to the times $T_1$, $T_2$, and $T_3$ from the pulse wave signal PS. Here, the local minimum point may refer to the smallest value of the secondary differential signal in a given interval (e.g., a systolic interval, or a diastolic interval), and may correspond to a specific point having a downward convex shape in the interval of the secondary differential signal which is observed to be decreased and then is increased again past the specific point. However, the characteristic point is not limited thereto, and the processor 120 may detect a local maximum point from the secondary differential signal, and may extract time and amplitude values corresponding to the detected local maximum point as characteristic points. The local maximum point may refer to the largest value of the secondary differential signal in a given interval (e.g., a systolic interval, or a diastolic interval), and may correspond to a specific point having an upward convex shape in the interval which is observed to be increased until the specific point and then is decreased past the specific point.

In another example, the processor 120 may obtain, as characteristic points, a time $t_{max}$ and an amplitude $P_{max}$, at which an amplitude has a maximum value in a specific interval of the pulse wave signal PS. In this case, the specific interval may refer to an interval between a starting point of the pulse wave signal PS and a point where a dicrotic notch (DN) appears, which indicates a systolic interval of blood pressure.

In yet another example, the processor 120 may obtain, as characteristic points, a duration $PPG_{dur}$ indicating the entire measurement time period of a bio-signal, or an area $PPG_{area}$ of a bio-signal waveform. In this case, the area under the bio-signal waveform may refer to the entire area under a bio-signal waveform, or an area under a bio-signal waveform corresponding to a predetermined percentage (e.g., 70%) of the total duration $PPG_{dur}$ of the bio-signal.

In still another example, the processor 120 may extract, as an additional characteristic point, an internally dividing point between the extracted two or more characteristic points. When an unstable waveform is generated in a pulse wave signal due to an abnormal environment such as motion noise, sleep, and the like, characteristic points may be extracted at wrong locations. The measurement of blood pressure may be supplemented by using the internally dividing point between the wrongly extracted characteristic points.

For example, upon extracting characteristic points ($T_1$, $P_1$) and ($T_{max}$, $P_{max}$) in the systolic interval, the processor 120 may calculate an internally dividing point ($T_{sys}$, $P_{sys}$) between the extracted characteristic points ($T_1$, $P_1$) and ($T_{ram}$, $P_{max}$). In this case, the processor 120 may apply a weighted value to time values $T_1$ and $T_{max}$ of the two characteristic points ($T_1$, $P_1$) and ($T_{max}$, $P_{max}$), and may calculate a time $T_{sys}$ of the internally dividing point by using each of the time values to which the weighted value is applied, and may extract an amplitude $P_{sys}$ corresponding to the time $T_{sys}$ of the internally dividing point. However, the internally dividing point is not limited thereto, and by analyzing the waveform of the obtained bio-signal, the processor 120 may further calculate an internally dividing point between the characteristic points $(T_1, P_1)$ and $(T_2, P_2)$ associated with the first and the second constituent pulse waveforms fw and $rw_1$ in the systolic interval of blood pressure, and an internally dividing point between the characteristic points $(T_3, P_3)$ and $(T_4, P_4)$ associated with the third and the fourth constituent pulse waveforms $rw_2$ and $rw_3$ in a diastolic interval of blood pressure, and the like.

The processor 120 may extract the first feature value and the second feature value by combining various characteristic points obtained from the bio-signal. For example, the processor 120 may extract the first feature value and the second feature value by multiplying, dividing, adding, and subtracting the plurality of characteristic points, or a combination thereof. Alternatively, the processor 120 may extract the first feature value and the second feature value by using a function having, as input values, values obtained by multiplying, dividing, adding, and subtracting the plurality of characteristic points or a combination thereof. Here, the function may be a linear function, a quadratic function, a polynomial function, a logarithmic function, or an exponential function, but is not limited thereto, and any other type of function may also be used. In yet another example, the processor 120 may extract the first feature value and the second feature value by using a function having at least one characteristic point as an input value, but is not limited thereto.

In addition, the processor 120 may extract the first feature value and the second feature value by combining characteristic points differently. Further, by combining characteristic points differently according to blood pressure values to be extracted, e.g., mean arterial pressure, systolic blood pressure, diastolic blood pressure, processor 120 may extract each characteristic point for each type of blood pressure measurements.

The processor 120 may calculate a first variation in the first feature value compared to a first reference feature value. Further, the processor 120 may calculate a second variation in the second feature value compared to a second reference feature value. For example, the first variation may increase as a ratio of the first feature value to the first reference value increases, and the second variation may increase as a ratio of the second feature value to the second reference value increases. In this case, the first reference feature value and the second reference feature value may refer to feature values associated with CO and TPR which are extracted from the bio-signal acquired at a reference time (e.g., a time of calibration or a time of a stable state including a time of an empty stomach state). For example, the processor 120 may calculate the first variation and the second variation by using the following Equation 2.

$$\Delta f_1 = \frac{f_{1cur}}{f_{1cal}} - 1$$ [Equation 2]

$$\Delta f_2 = \frac{f_{2cur}}{f_{2cal}} - 1$$

Herein, $\Delta f_1$ denotes the first variation, $f_{1cur}$ denotes the first feature value, $f_{1cal}$ denotes the first reference feature value, $\Delta f_2$ denotes the second variation, $f_{2cur}$ denotes the second feature value, and $f_{2cal}$ denotes the second reference feature value.

In addition, upon calculating the first variation and the second variation, the processor 120 may calculate a third variation based on the first variation and the second variation. For example, the processor 120 may calculate the third variation by multiplying the first variation by the second variation. In particular, the third variation may be a factor for correcting a blood pressure variation, which may not be reflected using only the first feature value and the second feature value under the condition of blood pressure change such as high-intensity aerobic exercise.

The processor 120 may estimate a blood pressure variation by combining the calculated first variation, second variation, and third variation. In particular, the processor 120 may multiply each of the first, the second, and the third variations by a combination coefficient, and may add up the multiplied variations. In this case, the processor 120 may obtain a blood pressure estimation result, in which characteristics of each user are reflected, by further applying a scaling factor to the result of combination. The following Equation 3 represents a blood pressure estimation equation, but the equation is not limited thereto.

$$\Delta BP = SF(\alpha \Delta f_1 + \beta \Delta_2 + \gamma \Delta f_3)$$ [Equation 3]

Herein, $\Delta BP$ denotes the estimated blood pressure variation; $\Delta f_1$, $\Delta f_2$, and $\Delta f_3$ each denote the first variation, the second variation, and the third variation; $\alpha$, $\beta$, and $\gamma$ each denote combination coefficients applied to each of the variations, and may be defined according to the types of blood pressure to be estimated and/or characteristics of a user; and SF denotes a scaling factor pre-defined according to characteristics of a user and/or the types of blood pressure to be estimated. For example, the scaling factor may be a reference MAP, a reference diastolic blood pressure (DBP), or a reference systolic blood pressure (SBP_ at a calibration time which are measured from a user by an external blood pressure measuring apparatus, or may be a value calculated by combining two or more thereof.

Upon estimating the blood pressure variation as described above, the processor 120 may estimate blood pressure by using a function as represented by the following Equation 4.

$$BP_{est} = BP_{cal} + \Delta BP$$ [Equation 4]

Herein, $BP_{est}$ denotes an estimated blood pressure value, $\Delta BP$ denotes an estimated blood pressure variation, and $BP_{cal}$ denotes a reference blood pressure at the time of calibration. In this case, blood pressure BP may refer to MAP, DBP, and SBP.

In an example embodiment, the processor 120 may independently estimate variations in MAP, DBP, and SBP by using the following Equations 3 and 4. For example, the first feature value and the second feature value may be extracted separately for each type of blood pressure. Alternatively, the processor 120 may independently estimate variations in MAP, DBP, and SBP by setting a combination coefficient and/or a scaling factor differently for each type of blood pressure.

In another example embodiment, the processor 120 may sequentially estimate MAP, DBP, and SBP. For example, the processor 120 may obtain an estimated MAP value by using the above Equations 3 and 4, and may estimate DBP and SBP sequentially by using the estimated MAP value. The processor 120 may estimate DBP and SBP by using a pulse pressure along with the estimated MAP value. In this case, the pulse pressure may be obtained by analyzing a bio-signal, a pulse pressure measured by a pulse pressure measuring device may be received, or a predetermined reference pulse pressure of a user may also be used. The following Equations 5 and 6 are examples of functions for estimating DBP based on the estimated MAP value and the pulse pressure.

$$DBP = MAP - \frac{PP}{3} \quad \text{[Equation 5]}$$

$$DBP = MAP - 0.01 \times \exp\left(4.14 - \frac{40.74}{HR}\right) \times PP$$

$$SBP = DBP + PP \quad \text{[Equation 6]}$$

Herein, MAP denotes mean arterial pressure, DBP denotes diastolic blood pressure, SBP denotes systolic blood pressure, PP denotes pulse pressure, and HR denotes heart rate.

Generally, vascular compliance of each individual varies depending on a cardiovascular health condition. When blood pressure changes or CO and TPR change in two blood vessels of different vascular compliances, a shape of pressure waves may be changed differently. When blood pressure is the same or when CO and TPR change according to vascular compliance, the waveform of PPG signal may be changed differently for each individual. As described above, when blood pressure is estimated by using the first feature value and the second feature value which are based on the waveform of a bio-signal, a variation in the first feature value and the second feature value may be different from a variation in the actual CO and TPR values.

Figure 3B:
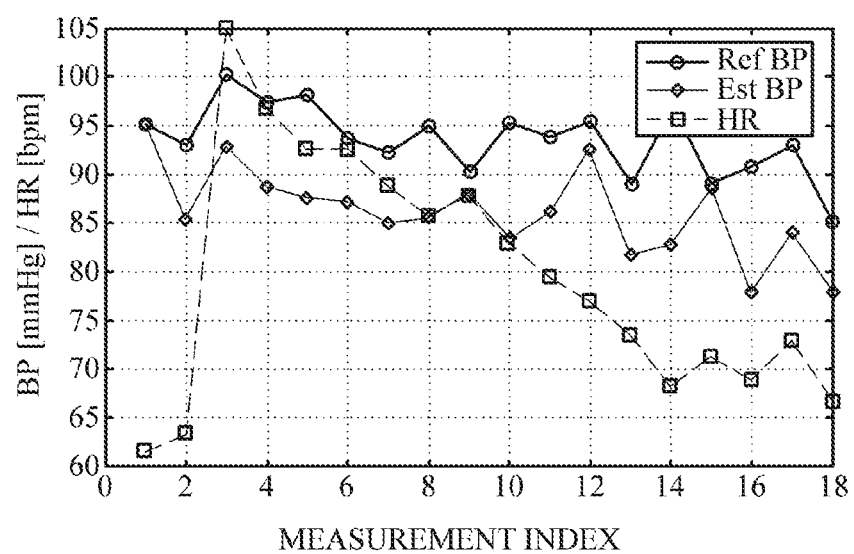
Figure 3C:
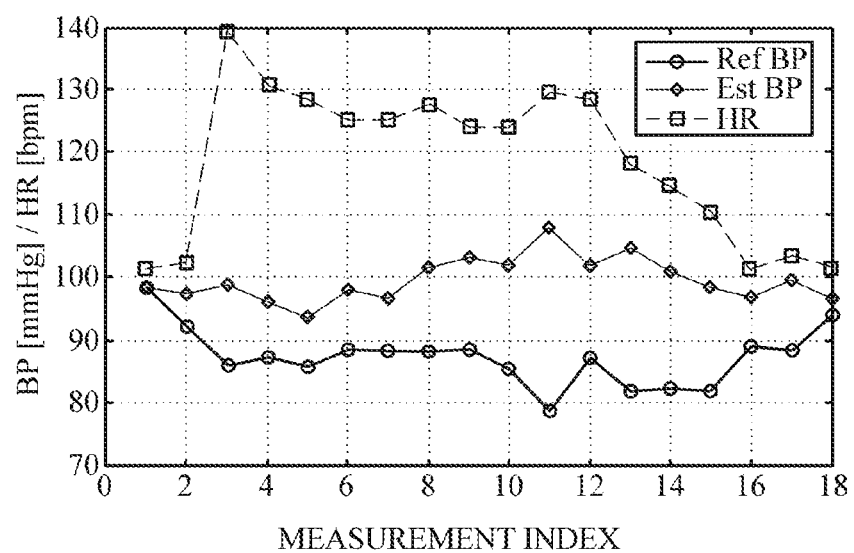

Referring to FIGS. 3B and 3C, in a blood pressure change mechanism associated with high-intensity aerobic exercise, a heart rate HR increases sharply in an interval of 2 to 4 of a measurement index. FIG. 3B illustrates an example where in the change mechanism, an estimated blood pressure value Est BP, which is estimated based on the first feature value and the second feature value, is measured lower than an actual blood pressure value Ref BP in the blood pressure change mechanism. Further, FIG. 3C illustrates an example where an estimated blood pressure value Est BP is measured higher than the actual blood pressure value Ref BP in the blood pressure change mechanism. As illustrated therein, when blood pressure is estimated without considering vascular compliance of each individual, errors may occur, such as the estimated blood pressure value measured higher or lower than the actual blood pressure value, even in the same blood pressure change mechanism.

Figure 3D:
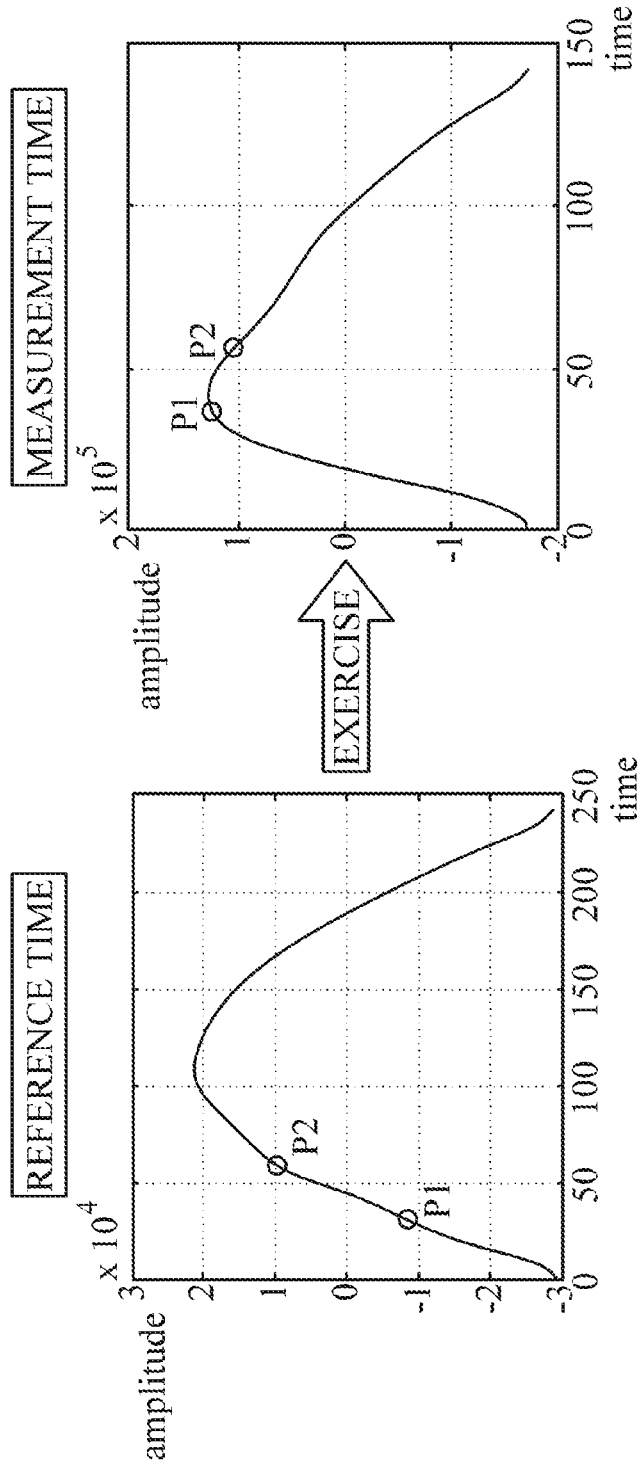
Figure 3E:
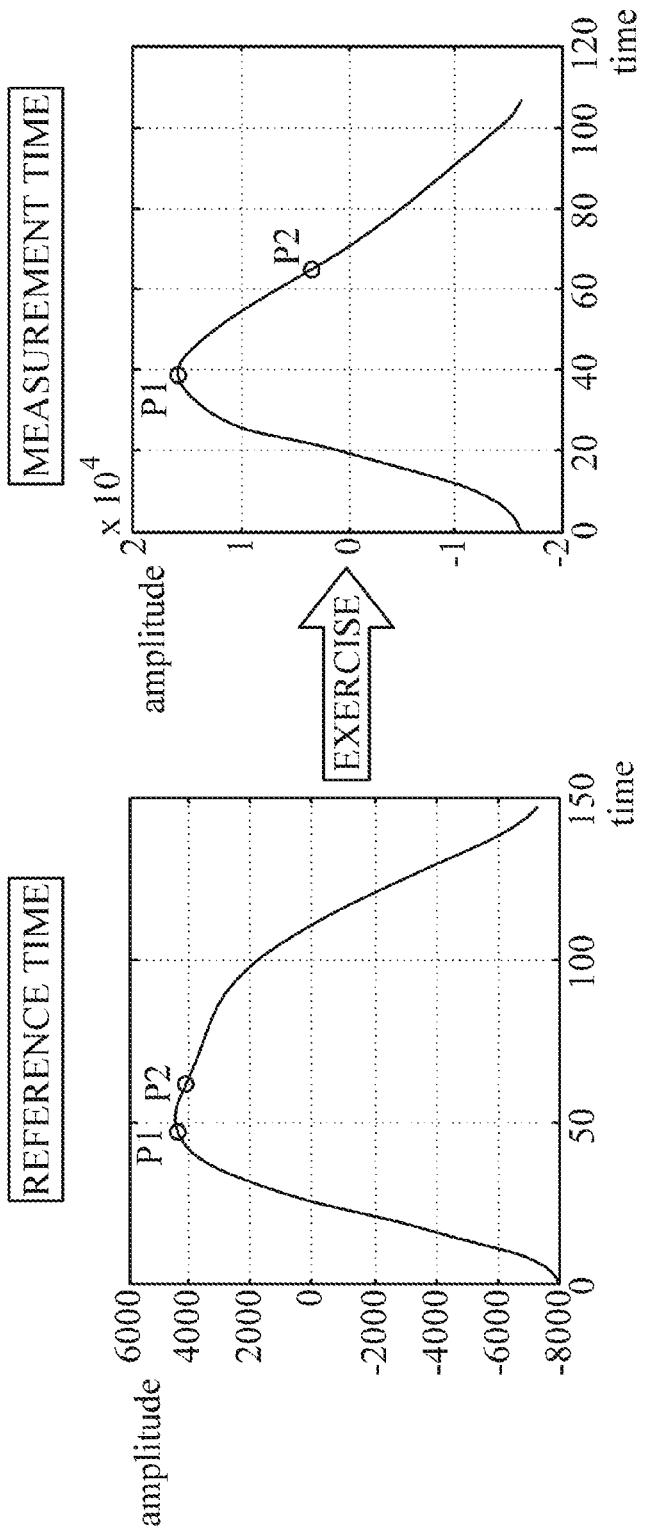

FIG. 3D illustrates a pulse wave signal in a condition showing the result of FIG. 3B. Referring to FIG. 3D, an amplitude P1 of a first pulse waveform component included in the pulse wave signal of a reference time may be observed at a lower position than an amplitude P2 of a second pulse waveform component. Then, referring to a pulse wave signal at a measurement time after exercise, the amplitude of the first pulse waveform component increases sharply. By contrast, FIG. 3E illustrates a pulse wave signal in a condition showing the result of FIG. 3C. Referring to FIG. 3E, the amplitude P1 of the first pulse waveform component included in the pulse wave signal of the reference time may be observed at a very high position. Then, referring to a pulse wave signal at a measurement time after exercise, it can be seen that the amplitude P1 of the first pulse waveform component hardly changes, but the amplitude P2 of the second pulse waveform component is significantly decreased.

As described above, referring to FIGS. 3B and 3E, an amplitude of each pulse waveform component included in the bio-signal of a time of a stable state (e.g., an amplitude of the first pulse waveform component) may be different for each individual, and may be related to vascular compliance of each individual. In the example embodiment, by reflecting the effect of vascular compliance of each individual in estimation of blood pressure using the first feature value and the second feature value, accuracy in estimating blood pressure may be improved.

For example, the processor 120 may obtain a reference value associated with vascular compliance, and may reflect an effect of vascular compliance of each individual in each feature value by adjusting combination coefficients α, β, and γ for each variation, which is described above in Equation 3, based on the obtained reference value. In this case, only a portion of each combination coefficient may be adjusted, but the combination coefficient is not limited thereto. For convenience of explanation, an example of adjusting a combination coefficient of the second feature value associated with TPR (hereinafter referred to as a "second combination coefficient") will be described below.

The processor 120 may obtain an adjustment value to adjust the second combination coefficient for the second feature value associated with TPR by using a pre-defined adjustment value estimation equation as represented by the following Equation 7. However, the adjustment value is not limited thereto, and the processor 120 may obtain an adjustment value to adjust a combination coefficient for another feature value by using the following Equation 7 or other function similar thereto.

$$\delta = \lambda \times \left(\frac{a}{b} - 1\right) + 1 \quad \text{[Equation 7]}$$

Here, δ denotes an adjustment value for adjusting the second combination coefficient; λ denotes a predetermined constant; a denotes a statistical value (e.g., a mean value) of reference values related to vascular compliance, which are obtained from a plurality of users, and may be a value pre-obtained through preprocessing; and b denotes a reference value of a specific user desired to estimate blood pressure.

Upon obtaining the adjustment value, the processor 120 may multiply the obtained adjustment value δ by the second combination coefficient β, and may combine variations by using the multiplied value (δ×β).

In addition, the processor 120 may obtain a reference value to be input into an adjustment value estimation equation at a reference time (e.g., a time of a stable state including a time of an empty stomach state, or a time of calibration). For example, the processor 120 may calculate, as a reference value, a ratio between a first amplitude value at a position of the first pulse waveform component and a second amplitude value at a position of the second pulse waveform component, which are included in a bio-signal of the reference time. In another example, the processor 120 may calculate, as a reference value, a ratio between the first amplitude value and a maximum amplitude value of the bio-signal of the reference time. Further, the processor 120 may calculate, as a reference value, a ratio between the first amplitude value and an amplitude at a local maximum point of a secondary differential signal of a bio-signal, an amplitude at a maximum point of a secondary differential signal, and the like. However, the reference value is not limited thereto, and the processor 120 may use a ratio between the first amplitude value and various other values as a reference value.

In yet another example, the reference value may include a vascular compliance index. The vascular compliance index may include an Augmentation Index (Aix). Here, the Aix refers to a value obtained by dividing a difference between a first systolic peak and a second systolic peak by a total peak, and it is known that the Aix reflects vascular compliance. The processor 120 may receive the Aix at a reference time from an external device which measures the Aix. Alternatively, the Aix may be measured similarly using pressure waves of the radial artery. In this case, the waveform of a pulse wave signal, which is measured from a body part such as a wrist, a finger, and the like, is highly relevant to pressure waves of the artery, such that the processor 120 may obtain the Aix by analyzing the waveform of the pulse wave signal obtained at the reference time.

Figure 3F:
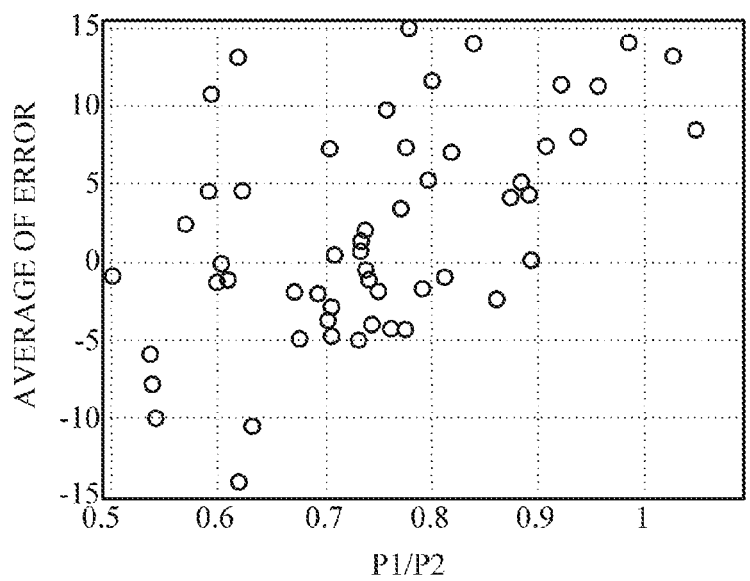
Figure 3G:
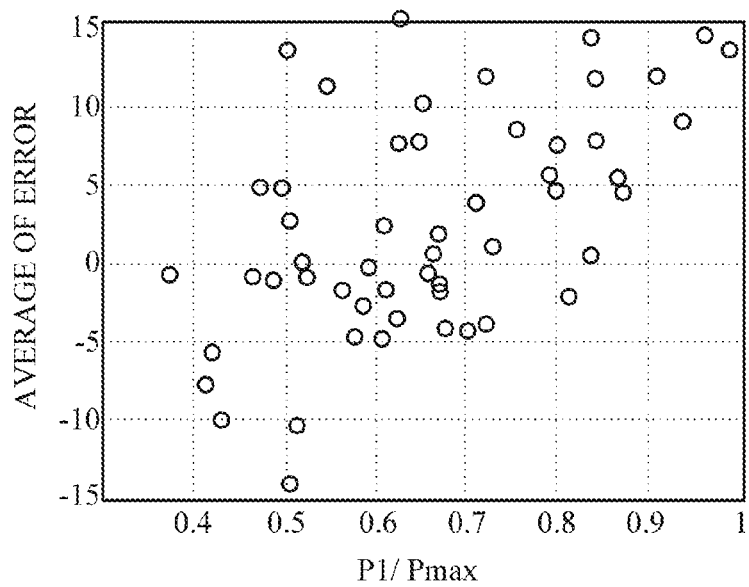

Referring to FIGS. 3F and 3G, an adjustment value calculation equation may be obtained by calculating a correlation between an average of errors, obtained from a plurality of users, and a reference value of each user. An average error value of each user may refer to an average value of errors between blood pressure values actually measured at a plurality of measurement times by each user and blood pressure values estimated using the first feature value and the second feature value. Further, the reference value may be a pre-defined value to be used as an input of the adjustment value calculation equation, and may refer to P1/P2, P1/Pmax, and the like as described above.

Referring back to FIG. 2, the blood pressure estimating apparatus 200 may further include a communication interface 210, an output interface 220, and a memory 230.

The communication interface 210 may communicate with an external device 250 by using wired or wireless communication techniques under the control of the processor 120, and may transmit and receive various data to and from the external device 250. For example, the communication interface 210 may transmit a blood pressure estimation result to the external device 250, and may receive various criteria required for estimating blood pressure from the external device 250. For example, the communication interface 210 may receive a reference blood pressure which is measured by a cuff-type blood pressure measuring device and the like, the vascular compliance index, the blood pressure estimation equation, the adjustment value estimation equation, and the like. In this case, examples of the external device 250 may include a cuff-type blood pressure measuring device, a device for measuring vascular compliance index, and an information processing device such as a smartphone, a tablet PC, a desktop computer, a laptop computer, and the like.

Examples of the communication techniques may include Bluetooth communication, Bluetooth Low Energy (BLE) communication, Near Field Communication (NFC), WLAN communication, Zigbee communication, Infrared Data Association (IrDA) communication, Wi-Fi Direct (WFD) communication, Ultra-Wideband (UWB) communication, Ant+ communication, WIFI communication, Radio Frequency Identification (RFID) communication, 3G communication, 4G communication, 5G communication, and the like. However, this is merely exemplary and is not intended to be limiting.

The output interface 220 may output results processed by the bio-information measurer 110 and the processor 120. For example, the output interface 220 may visually output an estimated bio-information value by using a display, or may output the information in a non-visual manner through voice, vibrations, tactile sensation, and the like by using a speaker, a haptic motor, a vibrator, and the like. The output interface 220 may divide a display area into two or more areas according to a setting, in which the output interface 220 may output a bio-signal graph, a blood pressure estimation result, and the like, which are used for estimating blood pressure, in a first area; and may output a blood pressure estimation history in the form of graphs in a second area. If an estimated blood pressure value falls outside a predetermined normal range, the output interface 130 may output warning information in various manners, such as highlighting an abnormal value in red and the like, displaying the abnormal value along with a normal range, outputting a voice warning message, adjusting a vibration intensity, and the like.

The memory 230 may store processing results of the bio-information measurer 110 and the processor 120. Further, the memory 230 may store various criteria required for estimating blood pressure. For example, the criteria may include user feature information such as a user's age, gender, health condition, and the like. In addition, the criteria may include various types of information, such as the reference blood pressure, the blood pressure estimation equation, a blood pressure estimation interval, the adjustment value estimation equation, and the like, but are not limited thereto.

The memory 230 may include at least one storage medium of a flash memory type memory, a hard disk type memory, a multimedia card micro type memory, a card type memory (e.g., an SD memory, an XD memory, etc.), a Random Access Memory (RAM), a Static Random Access Memory (SRAM), a Read Only Memory (ROM), an Electrically Erasable Programmable Read Only Memory (EEPROM), a Programmable Read Only Memory (PROM), a magnetic memory, a magnetic disk, and an optical disk, and the like, but is not limited thereto.

Figure 4:
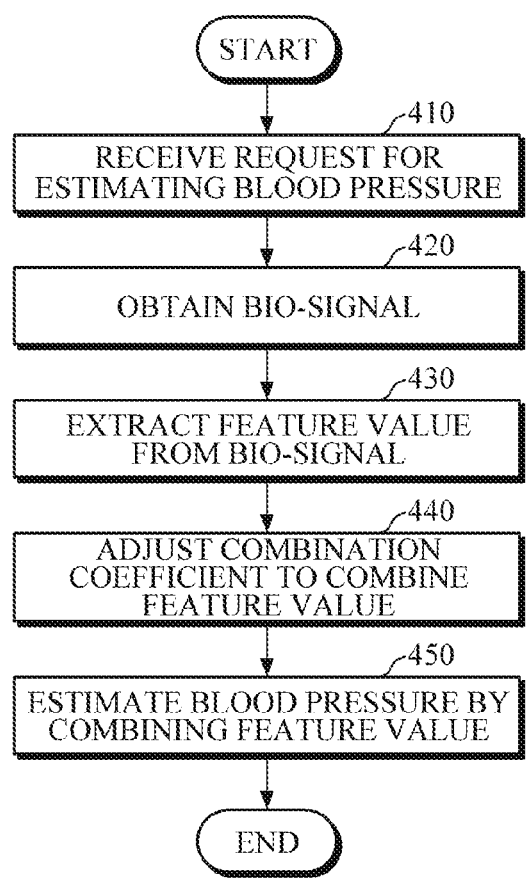
FIG. 4 is a flowchart illustrating a method of estimating blood pressure according to an example embodiment.

FIG. 4 is a flowchart illustrating a method of estimating blood pressure according to an example embodiment. The method of estimating blood pressure of FIG. 4 may be an example of a blood pressure estimating method according to the example embodiment of FIG. 1 or 2. Various example embodiments thereof are described above in detail, such that the description thereof will be briefly made below.

The blood pressure estimating apparatus 100/200 may receive a request for estimating blood pressure in operation 410. The blood pressure estimating apparatus 100/200 may provide an interface to a user, and may receive the request for estimating blood pressure input by the user through the interface. Alternatively, the blood pressure estimating apparatus 100/200 may communicate with an external device 250, and may receive the request for estimating blood pressure from the external device 250. In this case, the external device 250 may be a smartphone or a tablet PC carried by a user, and a user may control the operation of the blood pressure estimating apparatus 100/200 by using a device having excellent interface or computing performance.

Then, the blood pressure estimating apparatus 100/200 may obtain a bio-signal from an object in operation 420. Examples of the bio-signal may include various bio-signals, such as a PPG signal, an ECG signal, an EMG signal, a BCG signal, and the like.

Subsequently, the blood pressure estimating apparatus 100/200 may extract feature values by analyzing the obtained bio-signal in operation 430. In particular, the cardiovascular feature values may include a feature value associated with cardiac output and a feature value associated with total peripheral resistance. The blood pressure estimating apparatus 100/200 may extract feature values related to cardiac output and total peripheral resistance by analyzing a bio-signal, a differential signal obtained by differentiating the bio-signal, and the like, and by properly combining heart rate information, time and amplitude values of a maximum point of the bio-signal, time and amplitude values of a minimum point of the bio-signal, an area under a waveform of the bio-signal, amplitude and time values of pulse waveform components included in the bio-signal, and the like.

The blood pressure estimating apparatus 100/200 may adjust a combination coefficient to combine the extracted feature values for estimating blood pressure in operation 440. For example, the blood pressure estimating apparatus 100/200 may obtain a reference value associated with vascular compliance of a user based on a shape of a waveform of a bio-signal measured at a reference time, and may adjust a combination coefficient by using the reference value. For example, the blood pressure estimating apparatus 100/200 may obtain, as a reference value, a ratio between pulse waveform components included in the bio-signal, and may calculate an adjustment value for adjusting a combination coefficient by inputting the obtained reference value into a pre-defined adjustment value calculation equation. The reference value is not limited thereto, and various other indices which may reflect vascular compliance of a user may also be used.

The blood pressure estimating apparatus 100/200 may estimate blood pressure by combining the feature values in operation 450. For example, the blood pressure estimating apparatus 100/200 may normalize each feature value by dividing each feature value by a corresponding feature value of a reference time, and may calculate a variation in each feature value based on the result of normalization. Further, upon calculating the variation in each feature value, the blood pressure estimating apparatus 100/200 may estimate blood pressure by multiplying each calculated variation by a combination coefficient, or the adjusted combination coefficient if adjusted in operation 440, and combining the variations. In particular, the blood pressure estimating apparatus 100/200 may estimate blood pressure by multiplying a value, obtained by combining the variations, by a scaling factor.

Figure 5:
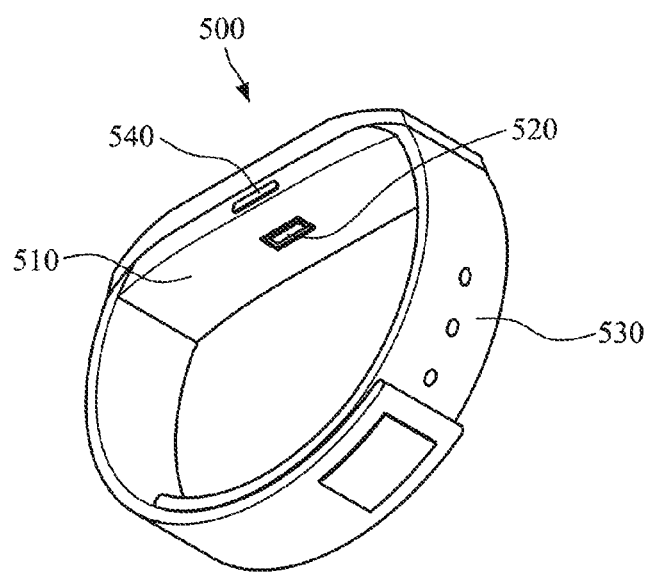
FIG. 5 is a diagram illustrating a wearable device according to an example embodiment.

FIG. 5 is a diagram illustrating a wearable device according to an example embodiment. Various example embodiments of the blood pressure estimating apparatus 100/200 described above may be mounted in a smart watch worn on a wrist or a smart band-type wearable device. However, the wearable device is not limited thereto, and may be mounted in a smartphone, a tablet PC, a desktop computer, a laptop computer, and the like.

Referring to FIG. 5, the wearable device 500 includes a main body 510 and a strap 530.

The main body 510 may be formed to have various shapes, and may include modules which are mounted inside or outside of the main body 510 to perform the aforementioned function of estimating blood pressure as well as various other functions. A battery may be embedded in the main body 510 or the strap 530 to supply power to various modules of the wearable device 500.

The strap 530 may be connected to the main body 510. The strap 530 may be flexible, so as to be bent around a user's wrist. The strap 530 may be bent in a manner that allows the strap 530 to be detached from the user's wrist or may be formed as a band that is not detachable. Air may be injected into the strap 530 or an airbag may be included in the strap 530, so that the strap 530 may have elasticity according to a change in pressure applied to the wrist, and the change in pressure of the wrist may be transmitted to the main body 510.

The main body 510 may include a bio-signal measurer 520 for measuring a bio-signal. The bio-signal measurer 520 may be mounted on a rear surface of the main body 510, which comes into contact with the upper portion of a user's wrist, and may include a light source for emitting light onto the skin of the wrist and a detector for detecting light scattered or reflected from the object. The bio-signal measurer 520 may be implemented as a spectrometer including the light source and the detector. The bio-signal measurer 520 may further include a contact pressure sensor for measuring contact pressure applied by the object.

A processor 120 may be mounted in the main body 510. The processor 120 may be electrically connected to various modules, mounted in the wearable device 500, to control operations thereof.

In addition, the processor 120 may estimate blood pressure by using the bio-signal measured by the bio-signal measurer 520. The processor 120 may obtain a feature value associated with CO and a feature value associated with TPR from the bio-signal. Further, the processor 120 may calculate variations in the feature values by normalizing each feature value with a feature value of a reference time, and may estimate blood pressure by combining the calculated variations. In particular, the processor 120 may obtain an additional feature value based on the feature value associated with CO and the feature value associated with TPR. The processor 120 may estimate blood pressure by multiplying the variations in each of the feature values by each combination coefficient, and combining the multiplied variations. In this case, in order to properly compensate for a feature value, which is greatly affected by vascular compliance of each individual, the processor 120 may obtain a reference value by analyzing a waveform of the bio-signal of the reference time, and may adjust a combination coefficient for a variation in the feature value, which is affected by vascular compliance, by using the reference value, thereby reflecting the effect of vascular compliance of each individual in estimation of blood pressure.

In the case where the processor 120 includes a contact pressure sensor, the processor 120 may monitor a contact state of the object based on contact pressure between the wrist and the bio-signal measurer 520, and may provide guidance on a contact position and/or a contact state to a user through a display.

Further, the main body 510 may include a memory 230 which stores a processing result of the processor 120 and various types of information. In this case, various types of information may include criteria for estimating blood pressure as well as information associated with functions of the wearable device 500.

In addition, the main body 510 may also include a manipulator 540 which receives a control command of a user and transmits the received control command to the processor 120. The manipulator 540 may include a power button to input a command to turn on/off the wearable device 500.

The display may be mounted on a front surface of the main body 510, and may include a touch panel for touch input. The display may receive a touch input from a user, may transmit the received touch input to the processor 120, and may display a processing result of the processor 120.

For example, the display may display the estimated blood pressure information. In this case, the display may display additional information, such as an estimation date of blood pressure, a user's health condition, and the like, along with the estimated blood pressure information. When a user requests detailed information by operating the manipulator 540 or by touching the display for touch input, the display may output detailed information in various manners.

Moreover, a communication interface, provided for communication with an external device such as a mobile terminal of a user, may be mounted in the main body 510. The communication interface may transmit an estimation result of bio-information to an external device, e.g., a user's smartphone, to display the result to a user. However, this is merely exemplary, and the communication interface may transmit and receive various types of necessary information.

Figure 6:
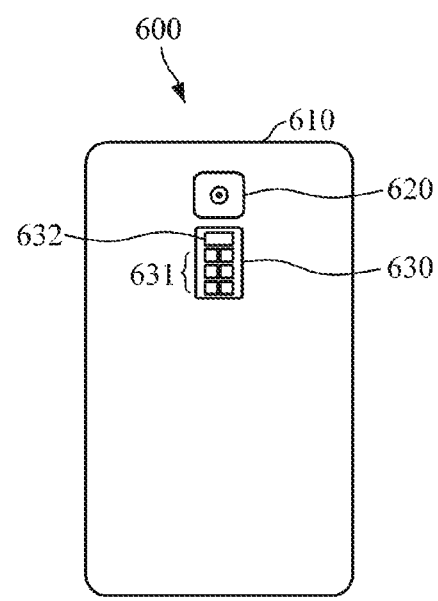
FIG. 6 is a diagram illustrating a smart device according to an example embodiment.

FIG. 6 is a diagram illustrating a smart device 600, to which embodiments of a blood pressure estimating apparatus are applied. In this case, the smart device may be a smartphone, a tablet PC, and the like.

Referring to FIG. 6, the smart device 600 includes a main body 610 and a bio-signal measurer 630 mounted on one surface of a main body 610. The bio-signal measurer 630 may include a pulse wave sensor which includes at least one or more light sources 631 and a detector 632. As illustrated in FIG. 6, the bio-signal measurer 630 may be mounted on a rear surface of the main body 610, but is not limited thereto. Further, the bio-signal measurer 630 may be configured in combination with a fingerprint sensor or a touch panel mounted on a front surface.

In addition, a display may be mounted on a front surface, of the main body 610. The display may visually display an estimation result of bio-information and the like. The display may include a touch panel, and may receive various types of information input through the touch panel and transmit the received information to the processor 120.

Moreover, an image sensor 620 may be mounted in the main body 610. When a user's finger approaches the bio-signal measurer 630 to measure a pulse wave signal, the image sensor 620 may capture an image of the finger and may transmit the captured image to the processor 120. Based on the image of the finger, the processor 120 may identify a relative position of the finger with respect to an actual position of the bio-signal measurer 630, and may provide the relative position of the finger to the user through the display, so as to guide measurement of pulse wave signals with improved accuracy.

The processor 120 may estimate blood pressure by using the bio-signal measured by the bio-signal measurer 630. As described above, the processor 120 may extract feature values related to cardiac output and total peripheral resistance from the bio-signal, and may estimate blood pressure by combining the extracted feature values. In this case, in order to compensate for a feature value which is affected by vascular compliance of each individual, the processor 120 may properly adjust a combination coefficient applied to the feature value, and then may combine the feature values, and detailed description thereof is made above.

While not restricted thereto, an example embodiment can be embodied as computer-readable code on a computer-readable recording medium. The computer-readable recording medium is any data storage device that can store data that can be thereafter read by a computer system. Examples of the computer-readable recording medium include read-only memory (ROM), random-access memory (RAM), CD-ROMs, magnetic tapes, floppy disks, and optical data storage devices. The computer-readable recording medium can also be distributed over network-coupled computer systems so that the computer-readable code is stored and executed in a distributed fashion. Also, an example embodiment may be written as a computer program transmitted over a computer-readable transmission medium, such as a carrier wave, and received and implemented in general-use or special-purpose digital computers that execute the programs. Moreover, it is understood that in example embodiments, one or more units of the above-described apparatuses and devices can include circuitry, a processor, a microprocessor, etc., and may execute a computer program stored in a computer-readable medium.

The foregoing exemplary embodiments are merely exemplary and are not to be construed as limiting. The present teaching can be readily applied to other types of apparatuses. Also, the description of the exemplary embodiments is intended to be illustrative, and not to limit the scope of the claims, and many alternatives, modifications, and variations will be apparent to those skilled in the art.

What is claimed is:

1. An apparatus for estimating blood pressure, the apparatus comprising:
    a photoplethysmogram (PPG) sensor configured to measure a bio-signal from a user; and
    a processor configured to:
        extract, from the bio-signal, one or more feature values comprising a first feature value that shows an increasing or decreasing trend in proportion to an actual cardiac output, and a second feature value that shows an increasing or decreasing trend in proportion to an actual total peripheral resistance,
        obtain a first variation in the first feature value compared to a first reference feature value, a second variation in the second feature value compared to a second reference feature value, and a third variation based on the first variation and the second variation, and
        estimate a blood pressure based on the first variation, the second variation, and the third variation.

2. The apparatus of claim 1, wherein the first reference feature value and the second reference feature value are obtained at a calibration time of the bio-signal or a time at which the user is in a stable state.

3. The apparatus of claim 1, wherein the processor is further configured to:
    obtain, as a reference value associated with vascular compliance, a maximum amplitude value of a reference bio-signal that is measured from the user at a reference time;
    obtain combination coefficients to be applied to the first variation, the second variation, and the third variation, respectively, based on the reference value associated with vascular compliance; and
    estimate the blood pressure by combining the first variation, the second variation, and the third variation to which the combination coefficients are applied.

4. The apparatus of claim 1, wherein the processor is further configured to:
    obtain a reference bio-signal including a first pulse waveform component and a second pulse waveform component, from the user at a reference time;
    obtain, as a reference value associated with vascular compliance, at least one of a ratio between a first amplitude value of the first pulse waveform component and a second amplitude value of the second pulse waveform component of the reference bio-signal, and a ratio between the first amplitude value and a maximum amplitude value of the reference bio-signal;
    obtain combination coefficients to be applied to the first variation, the second variation, and the third variation, respectively, based on the reference value associated with vascular compliance; and estimate the blood pressure by combining the first variation, the second variation, and the third variation to which the combination coefficients are applied.

5. The apparatus of claim 1, wherein the processor is further configured to:

obtain a reference value associated with vascular compliance that comprises a vascular compliance index including an Augmentation Index;

obtain combination coefficients to be applied to the first variation, the second variation, and the third variation, respectively, based on the reference value associated with vascular compliance; and estimate the blood pressure by combining the first variation, the second variation, and the third variation to which the combination coefficients are applied.

6. The apparatus of claim 5, wherein the processor is further configured to receive the vascular compliance index from an external device which measures the vascular compliance of the user.

7. The apparatus of claim 5, wherein the processor is further configured to obtain the Augmentation Index by analyzing a waveform of the reference bio-signal that is measured from the user at reference time.

8. The apparatus of claim 1, wherein the processor is further configured to:

obtain combination coefficients to be applied to the first variation, the second variation, and the third variation, respectively, based on a reference value associated with vascular compliance; and estimate the blood pressure by combining the first variation, the second variation, and the third variation to which the combination coefficients are applied.

9. The apparatus of claim 8, wherein the processor is further configured to obtain an adjustment value for adjusting the combination coefficients by inputting a statistical value of a plurality of reference values obtained from a plurality of other users, into a pre-defined adjustment value estimation equation.

10. The apparatus of claim 1, wherein the processor is further configured to obtain at least one information of heart rate information, an area under a waveform of the bio-signal, time and amplitude values of a maximum point of the bio-signal, time and amplitude values of a minimum point of the bio-signal, and amplitude and time values of pulse waveform components included in the bio-signal, and extract the one or more feature values based on the at least one information.

11. The apparatus of claim 1, wherein the processor is further configured to adjust a plurality of combination coefficients corresponding to the first variation, the second variation, and the third variation, and combine the first variation, the second variation, and the third variation by multiplying the first variation, the second variation, and the third variations by the adjusted plurality of combination coefficients, respectively.

12. The apparatus of claim 11, wherein the processor is further configured to estimate the blood pressure by applying a scaling factor to a resulting value of the combining the first variation, the second variation, and the third variation.

13. A method of estimating blood pressure, the method comprising:

measuring a bio-signal from a user;

extracting, from the bio-signal, one or more feature values comprising a first feature value that shows an increasing or decreasing trend in proportion to an actual cardiac output, and a second feature value that shows an increasing or decreasing trend in proportion to an actual total peripheral resistance;

obtain a first variation in the first feature value compared to a first reference feature value, a second variation in the second feature value compared to a second reference feature value, and a third variation based on the first variation and the second variation; and estimating a blood pressure based on the first variation, the second variation, and the third variation, and the one or more feature values extracted from the bio signal.

14. The method of claim 13, further comprising:

obtaining, as a reference value associated with vascular compliance, a maximum amplitude value of a reference bio-signal that is measured from the user at a reference time;

obtaining combination coefficients to be applied to the first variation, the second variation, and the third variation, respectively, based on the reference value associated with vascular compliance; and estimating the blood pressure by combining the first variation, the second variation, and the third variation to which the combination coefficients are applied.

15. The method of claim 13, further comprising:

obtaining a reference bio-signal including a first pulse waveform component and a second pulse waveform component, from the user at a reference time;

obtaining, as a reference value associated with vascular compliance, at least one of a ratio between a first amplitude value of the first pulse waveform component and a second amplitude value of the second pulse waveform component of the reference bio-signal, and a ratio between the first amplitude value and a maximum amplitude value of the reference bio-signal;

obtaining combination coefficients to be applied to the first variation, the second variation, and the third variation, respectively, based on the reference value associated with vascular compliance; and estimating the blood pressure by combining the first variation, the second variation, and the third variation to which the combination coefficients are applied.

16. The method of claim 13, further comprising obtaining combination coefficients to be applied to the first variation, the second variation, and the third variation, respectively, based on a reference value associated with vascular compliance; and estimating the blood pressure by combining the first variation, the second variation, and the third variation to which the combination coefficients are applied.

17. The method of claim 16, further comprising: obtaining an adjustment value for wherein the adjusting the combination coefficients by inputting a statistical value of a plurality of values obtained from a plurality of other users, into a pre-defined adjustment value estimation equation.

* * * * *